United States Patent [19]

Baldwin et al.

[11] 4,176,183

[45] Nov. 27, 1979

[54] NOVEL NAPHTHYRIDINES

[75] Inventors: John J. Baldwin; Gerald S. Ponticello, both of Lansdale, Pa.

[73] Assignee: Merck & Co., Inc., Rahway, N.J.

[21] Appl. No.: 925,577

[22] Filed: Jul. 17, 1978

Related U.S. Application Data

[63] Continuation-in-part of Ser. No. 792,752, May 2, 1977, abandoned.

[51] Int. Cl.$^2$ ............................ A61K 31/44; C07D 221/00
[52] U.S. Cl. ............................ 424/248.52; 424/250; 424/256; 544/111; 544/362; 546/123
[58] Field of Search .................... 260/296 AE, 296 N; 424/248.52, 250, 256; 544/111, 362; 546/123

[56] References Cited

U.S. PATENT DOCUMENTS

| | | | |
|---|---|---|---|
| 3,590,036 | 6/1971 | Lesher et al. | 260/296 N X |
| 3,641,152 | 2/1972 | Shavel, Jr. et al. | 260/296 AE X |
| 3,882,132 | 5/1975 | Lesher et al. | 260/296 N X |

OTHER PUBLICATIONS

Chemical Abstracts, Eighth Collective Index, pp. 20200S to 20201S, and Frontispage (received 1973).
Tonetti et al., Chemical Abstracts, vol. 85, abst. no. 21171b (1976).

*Primary Examiner*—John D. Randolph
*Attorney, Agent, or Firm*—Daniel T. Szura; Harry E. Westlake, Jr.

[57] ABSTRACT

Novel naphthyridines having a 3-amino-2-OR-propoxy substituent are disclosed. The compounds have β-adrenergic blocking and immediate onset antihypertensive activities.

25 Claims, No Drawings

NOVEL NAPHTHYRIDINES

This application is a continuation-in-part of U.S. application Ser. No. 792,752, filed May 2, 1977, now abandoned.

BACKGROUND OF THE INVENTION

The present invention concerns novel 3-amino-2-OR-propoxy substituted naphthyridines having useful pharmacological activity.

N-heteromonocyclic 3-amino-2-hydroxypropoxy substituted compounds having $\beta$-adrenergic blocking activity are known (U.S. Pat. No. 4,000,282; South African Pat. No. 74/01070) Mono-N-heterobicyclic 3-amino-2-hydroxypropoxy substituted compounds exhibiting $\beta$-adrenergic blocking effectiveness are known [Crowther et al., J. Med. Chem. 15, 260–266 (1972)].

Novel di-N-heterobicyclic compounds, namely 3-amino-2-OR-propoxynaphthyridines, have been discovered. The compounds have $\beta$-adrenergic blocking activity and antihypertensive activity of immediate onset.

SUMMARY OF THE INVENTION

Naphthyridine compounds having 3 substituted amino-2-OR-propoxy substituent and their pharmaceutical use.

DESCRIPTION OF THE PREFERRED EMBODIMENTS

An embodiment of the present invention is naphthyridine compounds having the formulae

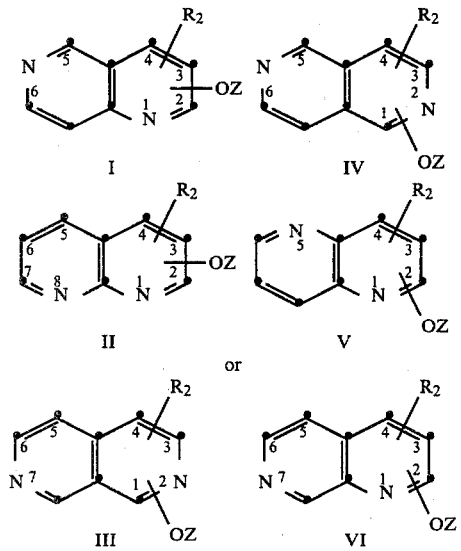

and pharmaceutically acceptable salts thereof wherein

Z is $-CH_2-CHOR-CH_2NHR_1$ wherein

R is hydrogen or $C_2-C_{12}$acyl and $R_1$ is $C_1-C_{12}$alkyl, and $R_2$ is H, Cl, Br, F, $-CN$, $-NH_2$, $CF_3$, $NO_2$
$-COOR_3$ wherein $R_3$ is H, $C_1-C_6$alkyl or $C_6-C_{12}$ carbocyclic aryl,
$-CONR_4R_5$ wherein $R_4$ and $R_5$ when separate, are H or $C_1-C_6$alkyl and when joined, are $-CH_2\mathbf{13}$ $(CH_2)_3-CH_2$, $-CH_2-CH_2-O-CH_2-CH_2$, $-CH_2-CH_2-NH-CH_2-CH_2-$, or $-CH_2-CH_2-N(CH_3)-CH_2-CH_2-$,
$-C_1-C_6$alkylthio, $-C_1-C_6$ alkylsulfinyl or
$-C_1-C_6$alkylsulfonyl.

The numbers within the naphthyridine formulae I–VI indicate the ring positions.

The pharmaceutically acceptable salts are the acid addition salts of the naphthyridine free base. Suitable acids include organic as well as inorganic acids. Examples of useful organic acids are carboxylic acids such as acetic acid, pamoic acid, maleic acid, succinic acid, citric acid, tartaric acid, oxalic acid, malic acid, pivalic acid, heptanoic acid, lauric acid, propanoic acid, pelargonic acid, oleic acid and the like, and non-carboxylic acids such as isethionic acid. Examples of useful inorganic acids are the hydrogen halides i.e. HCl, HBr, HI, phosphoric acid, sulfuric acid, and the like. The hydrohalide salts, especially the hydrochlorides and maleic acids, especially the hydrogen maleate, are preferred.

R may be hydrogen or $C_{2-12}$acyl. The $C_{2-12}$acyl groups include alkanoyl groups such as acetyl, pivaloyl, dodecanoyl, hexanoyl, succinoyl and the like—and carbocyclic aroyl groups such as benzoyl, 1- or 2-naphthoyl, p-methylbenzoyl, p-phenylbenzoyl and the like. The $C_2-C_6$ alkanoyl and benzoyl groups are preferred acyl groups. Hydrogen is a most preferred R group.

The $R_1$ substituent includes $C_1-C_{12}$alkyl groups and preferably the $C_1-C_6$alkyl groups. The alkyl groups are exemplified by methyl, $C_{12}H_{25}-$, hexyl, 2-ethylhexyl, isopropyl, sec-butyl, heptyl and the like. The $C_{3-4}$ branched chain alkyl $R_1$ groups are more preferred, with t-butyl being a most preferred group.

The $R_2$ substituent includes hydrogen, Cl, Br, $CF_3$, $NO_2$, F, $-CN$, $-NH_2$, the carboxy group and ester and amide derivatives thereof, the $C_1-C_6$alkyl-thio, sulfonyl and -sulfonyl derivatives thereof. The ester groups are $C_1-C_6$-alkylester exemplified by $-COOCH_3$, $-COOC_6H_{13}$, $-COOCH(CH_3)_2$, $-COOC_2H_5$ and the like and $C_6-C_{12}$ arylester, preferably carbocyclic aryl, exemplified by $C_6H_5-ooc-$, p-$CH_3-C_6H_5-OOC-$, $C_6H_5-C_6H_5-OOC-$, $C_{10}H_8-OOC-$ and the like. The amide groups include $-CONH_2$, $C_1-C_6$ substituted amide groups such as $-CON(CH_3)_2$, $-CON(C_6H_{13})_2$, $-CONHC_2H_5$, $-CON$ (sec.butyl)$_2$ and the like and carbonyl heterocyclic groups such as

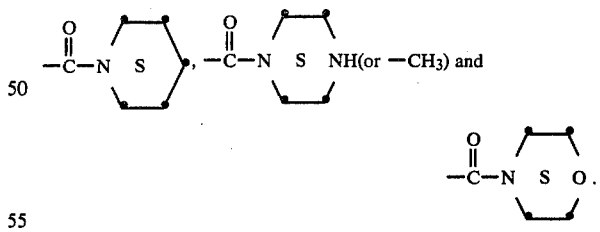

The $C_1-C_6$ alkyl-thio, -sulfinyl and -sulfonyl groups are exemplified by $CH_3-S-$, $C_6H_{13}-S-$, $(CH_3)_3C-S-$, $(CH_3)_2CH-SO-$, $CH_3-SO_2-$, $C_2H_5-SO_2-$, $C_6H_{13}-SO-$, $C_5H_{11}-SO-$, sec.-butyl-$SO_2-$ and the like. Of the $R_2$ groups CN is preferred.

The naphthyridine compounds have one chiral center which confers optical activity. The optical isomers are designated conventionally as L and D, l and d, + and −, S and R or by combinations of these symbols. Where the formula or compounds name herein carries no specific designation, the formula or name includes the individual isomers, the mixtures thereof and racemates.

Preferred naphthyridines are those having the —OZ group in a position ortho to a ring nitrogen. In more preferred naphthyridines, the $R_2$ substituent is also ortho to the —OZ group.

Particularly preferred naphthyridines are those of Formulae I, II and III. More particularly preferred are these naphthyridines wherein the —OZ group is ortho to the N atom, and especially where the $R_2$ group is ortho to the —OZ group.

Especially preferred naphthyridines have the formulae:

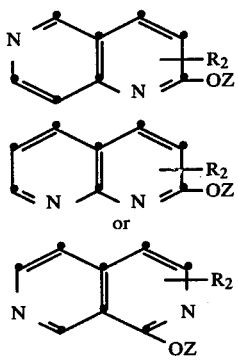

More preferred naphthyridines have the formulae

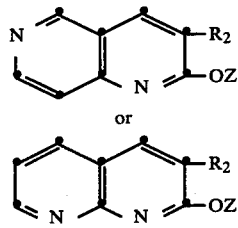

In the most preferred naphthyridines, $R_2$ is cyano and Z is —$CH_2$—CHOH—$CH_2$—$NR_1$ where $R_1$ is $C_1$-$C_6$alkyl, with $C_3$-$C_4$ branched alkyl as a preferred group with t-butyl being most preferred.

While the naphthyridines include all optical isomers and mixtures, the S-isomer form is preferred.

The naphthyridines of the present invention can be prepared by any convenient process.

One such process involves the coupling of a halonaphthyridine with a suitable substituted oxazolidine and hydrolyzing the reaction product obtained. This process is illustrated by the following set of reaction equations:

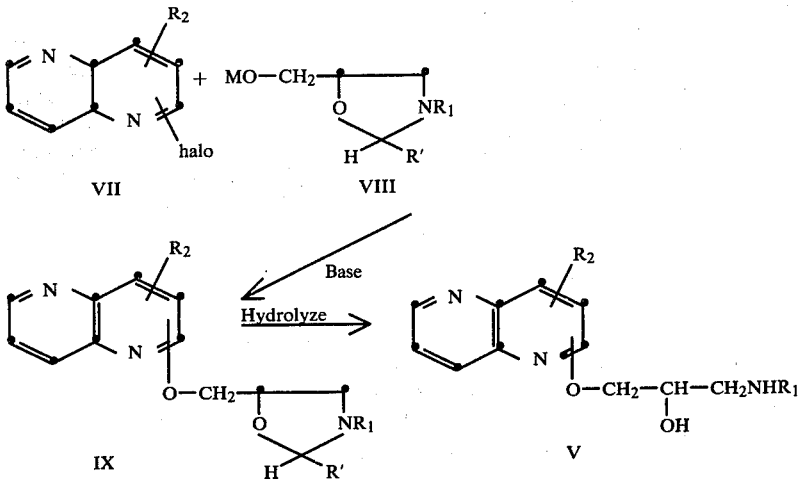

Halo may be Cl, Br and I, with Cl being preferred. M is an alkali metal, preferably potassium or sodium. $R_2$ is hydrogen or alkyl or residue of any suitable aldehyde

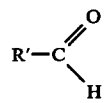

e.g. a $C_6$-$C_{12}$ arylaldehyde, such as benzaldehyde, naphthaldehyde, m-$NO_2$-benzaldehyde, p-phenylbenzaldehyde, tolualdehyde, and the like, furfural or a $C_2$-$C_{12}$ alkanal such as acetaldehyde, butyraldehyde,

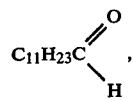

2-ethylhexanol and the like. The process for preparing oxazolidines where M is hydrogen (and related coupling reaction) is disclosed in U.S. Pat. No. 3,718,447 and U.S. Pat. No. 3,657,237 and to the extent necessary the pertinent disclosure is incorporated herein by reference. The alkali metal salt of the oxazolidine is prepared in a conventional manner by reaction of the corresponding hydroxymethyloxazolidine with an appropriate amount of an alkali base reactant. However, this reaction is more conveniently carried out with in-situ formation of the alkali matal oxazolidine salt (Formula VIII) by reacting the oxazolidine

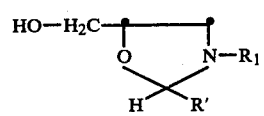

with the Formula VII naphthyridine in the presence of a suitable base such as $K_2CO_3$, an alkali metal alkoxide [e.g. K-O-C$+$(CH$_3$)$_3$], sodium hydride, an organolithium e.g. phenyllithium, n-butyllithium; lithium diisopropylamide and the like.

The coupling reaction can be carried out at temperatures ranging from about 0° to about 100° C. A temperature range of about 10° to about 50° C. is preferred. The reaction is generally carried out in a solvent. Any suitable solvent may be used. Examples of useful solvents are dioxane, toluene, tetrahydrofuran, dimethylformamide, toluene, dimethylsulfoxide, hexamethylphosphoramide, tert. butanol, acetone, alkanols and the like. The hydrolysis is carried out using conventional acid hydrolysis reagent and techniques e.g. treatment with a solution of any suitable acid such as $CH_3COOH$, HCl or $H_2SO_4$. The hydrolysis product can be directly obtained as the salt of the acid used for the hydrolysis. Ordinarily, the product is recovered as the free base after conventional neutralization of the salt.

The coupling reaction is ordinarily carried out at atmospheric pressure. Higher pressures may be used if desired.

When a racemic oxazolidine (Formula VII or X) is used as a reactant, the product is obtained as a racemate. The reacemate may be separated into its individual enantiomers by conventional resolution techniques.

When R' in the oxazolidine (e.g. Formulae VIII, IX or X) is other than hydrogen, in addition to the chiral center at oxazolidine position 5 there is a second chiral center at position 2. However, whenever the oxazolidine is designated as e.g. (S), (R) or (R,S), this designation refers only to the optical configuration around the carbon atom at the 5 position.

By using a single optical isomer of the Formula VII or X oxazolidine in the above reactions, the naphthyridine product may be obtained directly as a single enantiomer. Thus, if the S-isomer of the oxazolidine is used, then the product obtained will be the S-isomer. This provides a convenient way for directly preparing individual isomers of the present naphthyridines.

Naphthyridines of the present invention wherein R is other than hydrogen are conveniently prepared by treating the corresponding compound where R is hydrogen with an appropriate acylating agent such as an acyl halide, e.g. undecanoyl chloride, pivaloyl chloride, benzoylchloride, p-methoxybenzoyl chloride, an anhydride e.g. acetic anhydride, and the like. The reaction is illustrated by the following equation:

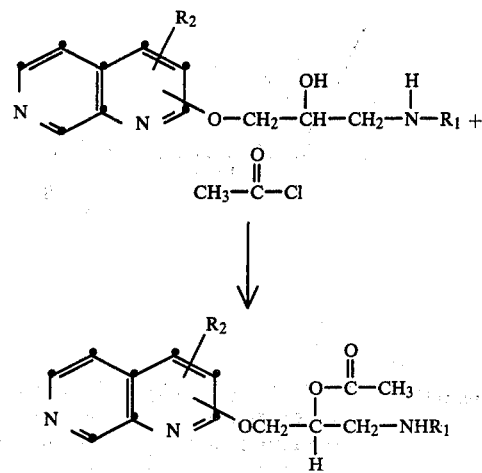

The compounds of the present invention also include the pharmaceutically acceptable salt of the novel naphthyridines. These salts are conveniently prepared e.g. by treating the naphthyridine with an appropriate amount of a useful acid, generally in a suitable solvent.

Additional processes for preparing naphthyridines with certain other substituents are illustrated by the following equation sequences. Conventional reaction conditions are employed. The desired other substituent is underlined.

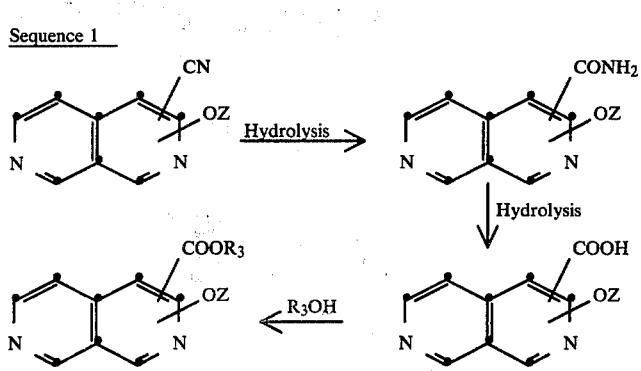

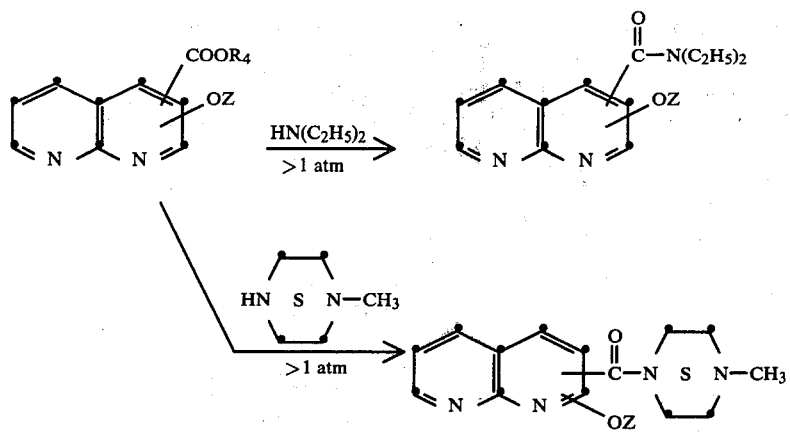

The naphthyridines having an alkylsulfinyl or alkylsulfonyl substituent are prepared by oxidizing the corresponding $C_1$–$C_6$ alkylthio containing compound. Any suitable oxidizing agent, e.g. $H_2O_2$, may be used. The following equation illustrates the reaction

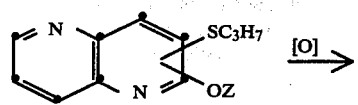 [O] →

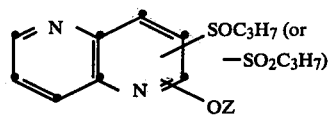

Certain naphthyridine intermediates are prepared using processes illustrated by the following reaction sequences. Conventional procedures and reagents are employed.

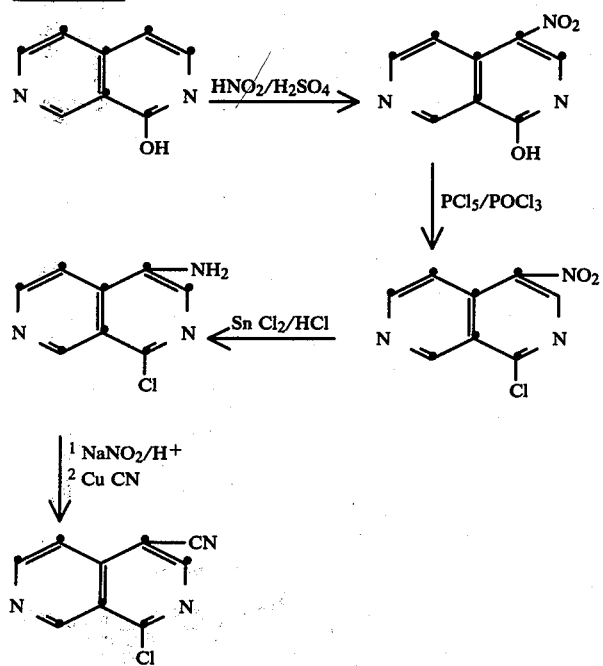

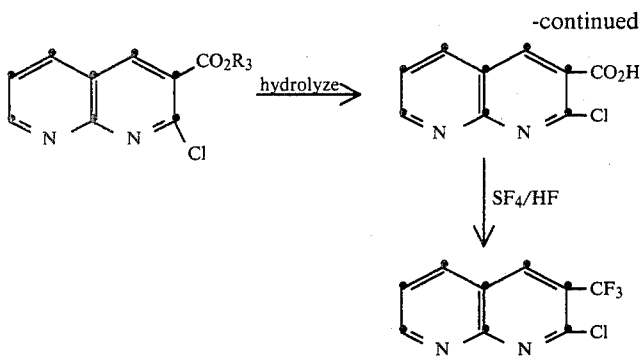

Sequence C

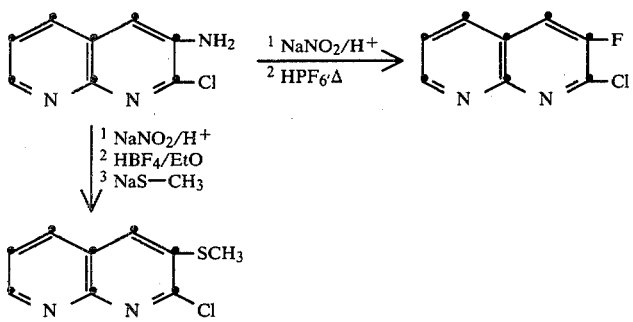

Sequence D

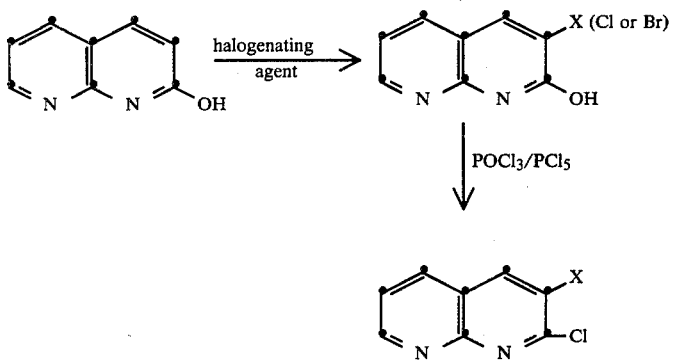

The compounds of the present invention have antihypertensive activity of rapid onset and are also β-adrenergic blocking agents. This antihypertensive activity is believed to be the result of peripheral vasodilation via a mechanism not directly related to β-adrenergic blockade. One advantage the present naphthyridines have over ordinary β-adrenergic agents is that the antihypertensive effect is immediate and generally of extended duration.

This rapid onset antihypertensive activity is determined by administering a representative compound of the present invention to spontaneously hypertensive (SH) rats and measuring the effect on blood pressure. Using this test method a representative naphthyridine was found to have this antihypertensive activity of immediate onset when administered orally.

The β-adrenergic blocking activity of the present naphthyridines is determined by measuring the ability of a representative compound to block isoproterenol induced β-adrenergic stimulant effects such as heart rate increase, hypotension and bronchodilation, in vivo. A representative naphthyridine was demonstrated to have β-adrenergic blocking activity, using this in-vivo test procedure.

The ability of the present naphthyridines to rapidly reduce blood pressure in an SH rat indicates that the present compounds are useful to treat hypertension in humans. Likewise, the observed β-adrenergic blocking activity of these compounds indicates that they are useful in humans as β-adrenergic blocking agents to therapeutically treat cardiovascular conditions such as angina pectoris, arrhythmia etc.

For use as antihypertensives and/or β-adrenergic blocking agents, the compounds of the present invention can be administered orally or parenterally i.e. intravenously, intraperitoneally, etc. and in any suitable dosage form. The compounds may be offered in a form (1) for oral administration e.g. as tablets in combination with other compounding ingredients (diluents or carriers) customarily used such as talc, vegetable oils, polyols, benzyl alcohols, starches, glycerine and the like—or dissolved, dispersed or emulsified in a suitable liquid carrier—or in capsules or encapsulated in a suitable encapsulating material; or (2) for parenteral administration, dissolved, dispersed, or emulsified in a suitable liquid carrier or diluent. The ratio of active ingredient (present naphthyridine) to compounding ingredient(s) will vary as the dosage form and pharmacelogical effect requires. Conventional procedures are used to prepare the pharmaceutical formulations.

The daily dosage level for the present compounds may be varied from about 0.02 mg. to about 50 mg. per kilogram of body weight. Daily doses ranging from about 0.05 to about 25 mg/kg are preferred, with about 0.1 to about 15 mg/kg being a more preferred range. Oral administration is preferred. Either single or multiple daily doses may be administered depending on unit dosage.

Thus, another embodiment of this invention is a pharmaceutical composition containing a therapeutically effective amount of a compound of the present invention.

The following examples illustrate the preparation of representative naphthyridines of the present invention. All parts are by weight unless otherwise noted. All temperatures are in °C. Some intermediates useful in preparing the present naphthyridines are disclosed in Hawes et al., J. Med. Chem. 16, 849–853 (1973).

EXAMPLE 1

A. 2-Hydroxy-3-cyano-1,8-naphthyridine

A mixture of 2-aminonicotinaldehyde (2.44 g., 0.02 m), ethyl α-cyanoacetate (4.52 g., 0.04 m.), absolute ethanol (50 ml.) and piperidine (0.5 ml) is stirred under reflux. After 1 hour, the solution is cooled to 0°–4° C. The yellow solid is filtered and dried to yield 2.5 g. (73%) of 2-hydroxy-3-cyano-1,8-naphthyridines, m.p. 300° C.

B. 2-Chloro-3-cyano-1,8-naphthyridine

A mixture of phosphorous pentachloride (12.2 g., 0.059 m.), phosphorous oxychloride (44 ml.), and 2-hydroxy-3-cyano-1,8-naphthyridine (2.3 g., 0.013 m.) is stirred under reflux. After 1 hour, the excess phosphorous oxychloride is distilled off under reduced pressure (20–30 mm). The residue is treated with ice and the solution neutralized with solid $Na_2CO_3$. The aqueous solution is extracted with $CHCl_3$ (3×100 ml.). The organic extracts are dried over $Na_2SO_4$, filtered and concentrated to dryness. The residue is sublimed at 140°–150° C. at 0.3 mm to yield 1.2 g. (81%) of 2-chloro-3-cyano-1,8-naphthyridine, m.p. 273° C.

C. (S) 3-Cyano-2-(3-tert. butylamino-2-hydroxypropoxy)-1,8-naphthyridine

Into a dry flask under $N_2$ is placed (S)-2-phenyl-3-tert. butylamino-5-hydroxymethyloxazolidine (2.4 g., 0.01 m.) dimethylformamide (15 ml.) and NaH (50% mineral oil 0.5., 0.01 m.) and the mixture heated for 5 minutes on a steam bath. After cooling to room temperature, 2-chloro-3-cyano-1,8-naphthyridine (1.89 g., 0.01 m.) is added and the solution is stirred at room temperature. After stirring overnight, the mixture is poured into $H_2O$ (200 ml.), and extracted with ether (4×100 ml.). The organic layer is washed with $H_2O$ (2×50 ml.) and cold 1 N HCl (2×100 ml.). The acid layer is poured into $NaOAc.3H_2O$ (27 g., 0.2 m.) and the solution stirred at room temperature. After 5 hours, the solution is extracted with ether (2×75 ml.). The aqueous layer is neutralized with saturated $Na_2CO_3$ and extracted with $CHCl_3$ (3×100 ml.). The organic layer is dried over $Na_2SO_4$, filtered and concentrated to dryness. The residue is crystallized from $CH_3CN$ to yield 0.85 g. (20%) of (S) 3-cyano-2-(3-tert.butylamino-2-hydroxypropoxy)-1,8-naphthyridine, m.p. 152°–3° C.

By using 2-chloro-3-cyano-1,6-naphthyridine in place of the 2-chloro-3-cyano-1,8 naphthyridine in Example 1, step C, (S) 3-cyano-2-(3-tert. butylamino-2-hydroxypropoxy)-1,6-naphthyridine is obtained.

EXAMPLE 2

(S) 3-Cyano-2-(3-tert. butylamino-2-hydroxypropoxy)-1,6-naphthyridine dihydrochloride Into a dry flask under $N_2$ is placed (S) 2-phenyl-3-tert. butylamino-5-hydroxymethyloxazolidine (4 g., 0.07 m.), DMF (25 ml.), and NaH (50% mineral oil 0.85 g., 0.018 m.) and heated on a steam bath for 5 minutes. After cooling to room temperature, 2-chloro-3-cyano-1,6-naphthyridine (3.3 g., 0.017 m.) is added and the mixture stirred at room temperature. After stirring overnight, the mixture is poured into $H_2O$ (200 ml.), and extracted with ether (4×100 ml.). The organic layer is washed with $H_2O$ (2×50 ml.), and cold 1 N HCl (2×100 ml.). The acid layer is poured in $NaOAc.3H_2O$ (27 g., 0.2 m.) and the solution is extracted with ether (2×75 ml.). The aqueous layer is neutralized with saturated $Na_2CO_3$ and extracted with $CHCl_3$, (3×100 ml.). The aqueous layer is dried over $Na_2SO_4$, filtered and concentrated to dryness. The residue is chromatographed on silica gel 60 and the product eluted with $CHCl_3$ saturated with aqueous $NH_3$. The crude product is crystallized from methanolic HCl and isopropanol (IPA) to yield 0.32 g. (5%) of (S) 3-cyano-2(3-tert. butylamino-2-hydroxypropoxy)-1,6-naphthyridine dihydro chloride, m.p. 215°–17° C.

By using (R,S) 2-methyl-3-isopropylamino-5-hydroxymethyloxazolidine in place of the (S) 2-phenyl-3-tert. butylamino-5-hydroxymethyloxazolidine in Example 2, the dihydrochloride of (R,S) 3-cyano-2-(3-isopropylamino-2-hydroxypropoxy)1,6-naphthyridine is obtained.

EXAMPLE 3

(S) 1-3(3-tert. Butylamino-2-hydroxypropoxy)-2,7-naphthyridine hydrogen maleate salt Into a dry flask under $N_2$ is placed (s)-2-phenyl-3-tert. butylamino-5-hydroxymethyloxazolidine (2.5 g., 0.01 m.), tert. butanol (50 ml.), potassium tert. butoxide (1.3 g., 0.011 m.) and 1-chloro-2,7-naphthyridine (1.67 g., 0.01 m.) and heated at 40° C. with stirring. After 15 hours, the solution is concentrated to dryness. Acetic acid (7.2 g., 0.12 m.) and $H_2O$ (120 ml.) are added to the residue and the solution stirred at room temperature. (2×100 ml.). The aqueous layer is neutralized with saturated $Na_2CO_3$ and extracted with $CHCl_3$ (3×100 ml.). The organic layer is dried over $Na_2SO_4$, filtered and concentrated to dryness. The residue is chromatographed on silica gel 60 and the product eluted with 20% MeOH—$CHCl_3$. The crude product is crystallized with maleic acid in IPA to yield 0.4 g. (10%) of (S) 1-(3-tert. butylamino-2-hydroxypropoxy)-2,7-naphthyridine hydrogen maleate salt, m.p. 177°–9° C.

Another process for preparing certain intermediates useful to prepare the naphthyridines of Formulae I–VI is illustrated by the following equation sequence:

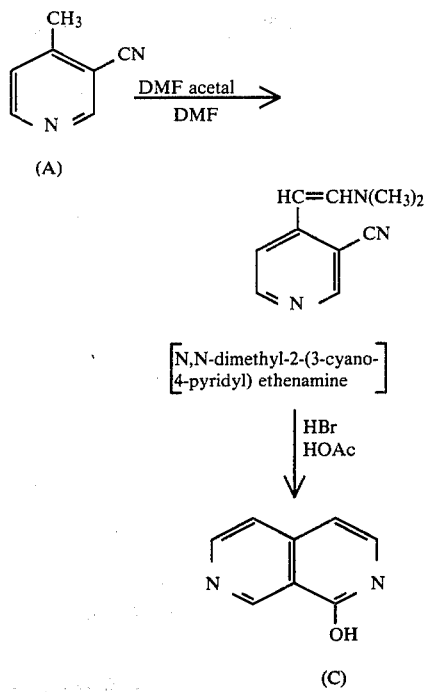

When the 2-methyl-3-cyanopyridine is substituted for 4-methyl-3-cyanopyridine (A) in the above reaction, the naphthyridine intermediate obtained is a mixture containing

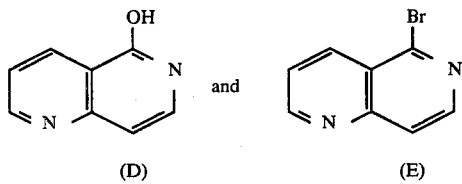

The hydroxy derivative (D) predominates. The following examples illustrate this preparation of intermediates—and their use in preparing the compounds of Formulae I–VI. All temperatures are in degrees Celsius.

EXAMPLE 4

A. N,N-dimethyl-2-(3-cyano-4-pyridyl)ethenamine

A solution of 4-methylnicotinonitrile (13.8 g, 0.12 m), dimethylformamide (DMF) (100 mL) and DMF acetal (14.0 g, 0.12 m) was heated at reflux under $N_2$. After 16 hours, the reaction mixture was concentrated at atmospheric pressure until the internal temperature reached 150°. The mixture was then cooled, poured into $H_2O$ (1 L) and extracted with $C_6H_6$(6×200 mL). The combined organic extracts were washed with $H_2O$ (2×200 mL), dried, filtered and evaporated to dryness. The residue was distilled at 150°–160° (0.2 mm) to yield 12.6 g (63%) of N,N-dimethyl-2-(3-cyano-4-pyridyl)ethenamine. An analytical sample was prepared by crystallization from $C_6H_6$—$C_6H_{14}$, mp 88°–90°.

B. Preparation of N,N-dimethyl-2-(3-cyano-2-pyridyl)ethenamine

N,N-dimethyl-2-(3-cyano-2-pyridyl)ethenamine was prepared using the procedure of 4 A from 2-methyl-3-cyanopyridine (9.0 g, 0.076 m), DMF acetal (11.0 g, 0.092 m) and DMF (50 mL) yielding N,N-dimethyl-2-(3-cyano-2-pyridyl) ethenamine b.p.=133°–135° (0.3 mm), m.p.=49°–50° after sublimation at 50° (0.3 mm).

C. Preparation of N,N-dimethyl-2-(2-cyano-3-pyridyl)ethenamine

A solution of 3-methyl-2-cyanopyridine (20.0 g, 0.17 m), DMF (200 mL) and DMF acetal (30 mL, 0.25 m) was heated at 120° with stirring under $N_2$ for 5 days. Additional acetal was periodically added in 5 mL aliquots (total 45 mL, 0.38 m). The solution was then evaporated to dryness to give a crude oil which solidified on standing. The solid was crystallized from ligroin to yield 16.5 g (56%) of N,N-dimethyl-2-(2-cyano-3-pyridyl)ethenamine. An analytical sample was prepared by recrystallization from ligroin, mp 71.5°–72°.

EXAMPLE 5

A. Preparation of 5-Hydroxy-1,6-naphthyridine and 5-Bromo-1,6-Naphthyridine A solution of 30% HBr in AcOH (200 mL) was added dropwise with mechanical stirring at 40° to a solution of N,N-dimethyl-2-(3-cyano-2-pyridyl)ethenamine (10.8 g, 0.062 m) in AcOH (100 mL). After the addition, the slurry was stirred at 55° for 2 hours. The mixture was then evaporated to dryness and the residue treated with ice and saturated aqueous $Na_2CO_3$. The aqueous layer was filtered and the filtrate extracted with $Et_2O$. The aqueous layer was placed in a continuous extractor with $CHCl_3$ to yield 7.0 g of a crude product. Sublimation of this product at 160°–180° (0.1 mm) yielded 5.1 g (56%) of hydroxy-1,6-naphthyridine. An analytical sample was prepared by crystallization from $CH_3OH$: m.p. 243–244.5.

The ether layer from above was dried, filtered, and evaporated to dryness. The residue was covered with $C_6H_{14}$ and filtered to yield 2.4 g of a crude product. Sublimation of this product at 70°–80° (0.1 mm) gave 1.9 g (15%) of 5-Bromo-1,6-naphthyridine; m.p. 112°–13°.

B. Preparation of 1-hydroxy-2,7-naphthyridine 1-hydroxy-2,7-naphthyridine was prepared using the procedure of 5 A from N,N-dimethyl-2-(3-cyano-4-pyridyl) ethenamine (3.0 g, 0.017 m), 30% HBr—HOAc (60 mL) and HOAc (30 mL). Yield of 1-hydroxy-2,7-naphthyridine was 1.58 g (64%) sublimation 170°–180° (0.1 mm). An analytical sample was prepared by crystallization from isopropanol; m.p.=260°–62°.

C. Preparation of 8-hydroxy-1,7-naphthyridine 8-hydroxy-1,7-naphthyridine was prepared using the procedure of 5 A. from N,N-dimethyl-2-(2-cyano-3-pyridyl) ethenamine (14.2 g, 0.082 m), 30% HBr—HOAc (150 mL) and HOAc (75 mL). Yield of 8-hydroxy-1,7-naphthyridine was 0.6 g (5%), sublimation 180°–200° (0.1 mm). An analytical sample was prepared by crystallization from $CH_3OH$; mp 236°–39°.

EXAMPLE 6

A. 5-(3-tert. Butylamine-2-hydroxypropoxy)-1,6-naphthyridine maleate salt

Into a dry flask under $N_2$ is placed (S)-3-tert. butylamine-5-hydroxymethyl-2-phenyloxazolidine (0.9 g, 0.004 m), tert. butanol (30 mL) and K(0.15 g, 0.004 m) and the mixture stirred at 40° C. After the K metal reacted, 5-bromo-1,6-naphthyridine (0.69 g, 0.0033 m)

was added and heated at 50° C. After 15 hours, the reaction mixture was poured into H₂O and extracted with Et₂O. The organic layer was washed with H₂O, 1 N HCl (100 mL) and the acid layer added to NaOAc—3H₂O (13.6 g, 0.1 m). After 5 hours, the solution was extracted with Et₂O, neutralized with saturated Na₂CO₃ and extracted with CHCl₃. The organic layer was dried, filtered and concentrated to dryness. The residue was crystallized as the maleate salt from EtOH-Et₂O to yield (S) 5-(3-tert. butylamino-2-hydroxypropoxy)-1,6-naphthyridine maleate salt (0.79 g; 59%) m.p. 192°–3° C.

EXAMPLE 7

A. 8-(3-tert. Butylamine-2-hydroxypropoxy)-1,7-naphthyridine maleate salt

Using the procedure of Example 6, (S) 3-tert.-butyl-5-hydroxymethyl-2-phenyloxazolidine (2.35 g, 0.01 m), tert.butanol (90 ML), K (0.39 g, 0.01 m) and 8-chloro-1,7-naphthyridine are allowed to react. After workup, the residue is crystallized as the maleate salt to yield (S) 8-(3-tert. butylamine-2-hydroxypropoxy)-1,7-naphthyridine.

Claims to the invention follow.
What is claimed is:

1. A compound having the formula and pharmaceutically acceptable salts thereof wherein Z is —CH₂—CHOR—CH₂—NHR₁ wherein
R is hydrogen or C₂–C₁₂ acyl and
R₁ is C₁–C₁₂alkyl, and
R₂ is H, Cl, Br, F, CN, —NH₂, NO₂, CF₃,
—COOR₄ wherein R₄ is H, C₁–C₆alkyl or C₆–C₁₂carbocyclic aryl,
—CONR₅R₆ wherein R₅ and R₆ when separate, are H or C₁–C₆alkyl and when joined, are —CH₂—(CH₂)₃—CH₂, —CH₂—CH₂—O—CH₂—CH₂—, —CH₂—CH₂—NH—CH₂—CH₂—, or —CH₂—CH₂—N(CH₃)—CH₂—CH₂—, —C₁–C₆alkylthio, —C₁–C₆ alkylsulfinyl or —C₁–C₆alkylsulfonyl.

2. A compound of claim 1 wherein R is H.
3. A compound of claim 2 wherein —OZ is in a position ortho to an N atom.
4. A compound of claim 3 wherein R₂ is ortho to the —OZ group.
5. A compound of claim 1 having the formula 6. A compound of claim 5 wherein R is hydrogen.
7. A compound of claim 6 wherein R₁ is C₃–C₄ branched alkyl.
8. A compound of claim 7 wherein R₁ is t-butyl.
9. The compound of claim 8 having the S-isomer configuration.
10. A compound of claim 5 having the formula 11. A compound of claim 10 wherein R is H, R₁ is C₃–C₄alkyl and R₂ is —CN.
12. A compound of claim 11 wherein —R₁ is t-butyl.
13. A compound of claim 12 having the S-isomer configuration.
14. A compound of claim 5 having the formula 15. A compound of claim 14 wherein R is hydrogen, R₁ is C₃₋₄alkyl and R₂ is —CN.
16. A compound of claim 15 wherein R₁ is t-butyl.
17. A compound of claim 16 having the S-isomer configuration.
18. A compound of claim 5 having the formula 19. A compound of claim 18 wherein R is H.
20. A compound of claim 19 where R₁ is t-butyl.
21. A compound having the formula of claim 1 wherein Z is an oxazolidine group of the formula wherein R₁ is C₁–C₁₂alkyl and R' is H, C₁–C₁₂alkyl or C₆–C₁₂aryl.

22. A pharmaceutical composition useful for effecting β-adrenergic blockade or treating hypertension containing an effective amount of a compound of claim 1.

23. A compound of claim 1 having the formula
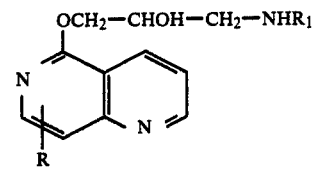
24. A compound of claim 23 where R is H and $R_1$ is tert. butyl.
25. A compound of claim 24 having the S-isomer configuration.